US012534832B2

(12) United States Patent
Lechner

(10) Patent No.: US 12,534,832 B2
(45) Date of Patent: Jan. 27, 2026

(54) METHOD FOR PRODUCING A COMPRESSION KNITTED FABRIC FOR PROSTHETIC STOCKINGS

(71) Applicant: Julius Zorn Inc., Cuyahoga, OH (US)

(72) Inventor: Siegfried Lechner, Schrobenhausen (DE)

(73) Assignee: Julius Zom Inc., Cuyahoga Falls, OH (US)

( * ) Notice: Subject to any disclaimer, the term of this patent is extended or adjusted under 35 U.S.C. 154(b) by 38 days.

(21) Appl. No.: 18/236,455

(22) Filed: Aug. 22, 2023

(65) Prior Publication Data

US 2024/0060220 A1 Feb. 22, 2024

(30) Foreign Application Priority Data

Aug. 22, 2022 (DE) ..................... 10 2022 121 165.7

(51) Int. Cl.
*D04B 1/26* (2006.01)
*A61F 2/78* (2006.01)
(Continued)

(52) U.S. Cl.
CPC .............. *D04B 1/26* (2013.01); *A61F 2/7812* (2013.01); *D04B 1/18* (2013.01); *A41B 11/003* (2013.01);
(Continued)

(58) Field of Classification Search
CPC . D04B 1/26; D04B 1/265; D04B 1/18; D04B 2331/10; D04B 2509/00; A61F 2/7812; A61F 2002/7818; A61F 13/08
(Continued)

(56) References Cited

U.S. PATENT DOCUMENTS 3,167,938 A * 2/1965 Seiler ..................... D04B 15/02 66/70
3,256,715 A * 6/1966 Monday ................... D04B 1/26 66/133
(Continued)

FOREIGN PATENT DOCUMENTS

DE 32 03 028 A1 8/1983
DE 197 43 074 A1 4/1999
DE 20 2017 103 246 U1 9/2018

OTHER PUBLICATIONS

Result of Examination Report for German Patent Application No. 10 2022 121 165.7, filed Aug. 22, 2022.

*Primary Examiner* — Alissa J Tompkins
*Assistant Examiner* — Dakota Marin
(74) *Attorney, Agent, or Firm* — Fleit Intellectual Property Law; Paul D. Bianco; Katharine Davis Wong

(57) ABSTRACT

A method for producing tubular compression knitted fabric includes: knitting a tubular first section of a basic knitted fabric forming stitches from at least one knitting yarn along a knitting direction, with a plurality of rows of stitches following one another in the knitting direction and an elastic weft yarn bound into the stitches via tuck stitches; and seamlessly knitting of a second section onto the first section along the knitting direction. In the second section viewed in the knitting direction, the number of stitches is successively reduced at least in some of the successive rows of stitches by transferring of stitches, thereby forming a closed dome-shaped end at the distal end of the second section by a reduction of stitches. The compression knitted fabric is usable to create prosthetic stockings for an amputated limb to apply compression pressure with a defined pressure profile without causing skin irritation.

7 Claims, 6 Drawing Sheets

(51) Int. Cl.
*D04B 1/18* (2006.01)
*A41B 11/00* (2006.01)
*A61F 13/08* (2006.01)

(52) U.S. Cl.
CPC ....... *A61F 2002/7818* (2013.01); *A61F 13/08* (2013.01); *D04B 1/265* (2013.01); *D10B 2331/10* (2013.01); *D10B 2509/00* (2013.01)

(58) Field of Classification Search
USPC ............................. 66/178 A, 70, 46, 30, 189
See application file for complete search history.

(56) References Cited

U.S. PATENT DOCUMENTS

| | | | | |
|---|---|---|---|---|
| 3,785,173 | A * | 1/1974 | Hanney | D04B 9/56<br>66/172 R |
| 4,548,057 | A | 10/1985 | Essig | |
| 6,158,253 | A * | 12/2000 | Svoboda | A61F 13/08<br>66/178 R |
| 6,196,030 | B1 | 3/2001 | Stoll | |
| 7,363,778 | B2 * | 4/2008 | Pickering | A61F 2/78<br>66/189 |
| 10,689,785 | B2 | 6/2020 | Buchschuster | |
| 2020/0179176 | A1 * | 6/2020 | Lechner | D04B 1/28 |

* cited by examiner

METHOD FOR PRODUCING A COMPRESSION KNITTED FABRIC FOR PROSTHETIC STOCKINGS

FIELD OF THE INVENTION

The invention relates to a method for producing a compression knitted fabric for producing prosthetic stockings supplying a compressive effect on an amputated limb of a patient, and to a compression knit for producing prosthetic stockings.

BACKGROUND

Prosthetic stockings for application to amputated limbs (limb stockings) are known in the prior art, wherein the prosthetic stockings are formed from a compression knit which exerts a compressive effect on an amputated limb of a patient in order to therapeutically compress the limb stump. Such a compression therapy can suppress swelling of the limb stump caused by edema. To avoid obstructing blood circulation in the limb stump, the compression pressure exerted by the prosthetic stocking must be precisely adjusted. To promote the lymphatic system in the limb stump, a pressure profile with a gradually decreasing compression pressure from the distal end of the limb stump is preferred. At the open proximal end of the prosthetic stocking, the compression knitted fabric thus generates a lower compression pressure than at the closed distal end.

Known compression knitted fabrics used for the production of compression stockings are knitted, for example, as circular knits on circular knitting machines. Thereby, the production of the dome-shaped end at the distal end of the stocking is problematic. For this purpose, a round opening is left at the distal end of the circular knitted compression stocking, which is closed, for example, by a circular pad or a knitted end cap by sewing on the circular pad or the knitted end cap. Due to the seam required for this, a thickening occurs at the distal end of the stocking, which distorts the gradual progression of the compression pressure and leads to friction between the stocking and the limb stump and thus to skin irritations on the limb.

Also known from the state of the art are compression knits for prosthetic stockings consisting of two flat knitted parts, each knitted on a flat knitting machine, which are sewn together along a longitudinal seam at their side edges. Here, the longitudinal seams impair the desired pressure distribution and causes skin irritation on the limb as well, and the longitudinal seams are perceived by the patient as annoying.

To avoid these disadvantages in circular knitted prosthetic stockings or stockings composed of two flat knitted parts, compression knits have been proposed in the prior art which can be produced seamlessly on a flat knitting machine with two opposing needle beds. Such a compression knit is known from U.S. Pat. No. 7,363,778 B2, which discloses a stretchable fabric sleeve that can be received on an amputated limb and has a distal end that conforms to the amputated limb. The stretchable fabric sleeve substantially comprises a unitary receptacle for the amputated limb, the receptacle substantially comprising a tubular section and a rounded end section. In particular, the rounded end section includes opposing panels knitted in series with a plurality of knitted short rows that create a progressive taper from an open edge of the tubular section to the proximal toe end of the end portion. The progressive taper of the knitted panels allows the outermost edge of the rounded end section to assume a rounded shape that comfortably conforms to an amputated limb and has no seams that would otherwise irritate the sensitive end of the amputated limb.

Known compression knits for amputated limbs (or for manufacturing prosthetic stockings) are knitted from an elastic knitting thread, e.g. a wound thread with an elastic elastane core thread, in order to produce a stretchable knit which can expand when applied to an amputated limb and thus exert a compression pressure depending on the stretch. However, it is difficult to precisely set a desired compression pressure and particularly to generate a gradual pressure profile with a decreasing compression pressure from the distal end of the stocking to the proximal end. The compression pressure generated by the compression knit on the limb of a patient depends on the stretch of the knitted fabric in the circumferential direction of the limb. The stretch in turn depends on the exact shape of the limb, in particular the course of the limb circumference along the longitudinal direction of the limb, and on the knitted weave of the knitted fabric. Therefore, the knitting of the distal end of the prosthetic stocking with a dome-shaped closed end of the knitted fabric without a seam and supplying a high compression pressure by the stocking onto the amputated limb of a patient is difficult to achieve.

SUMMARY OF THE INVENTION

Based on this background, one aspect of the invention relates to a method for the production of a compression knit for knitted prosthetic stockings for exerting a compressive effect on an amputated limb of a patient. The compression knit thereby shall enable to produce prosthetic stockings which can be worn comfortably in an efficient manner without causing skin irritations on the patient's limb and which generate an individually adjustable compression pressure with a gradual pressure profile, which can be individually adapted to the shape of the amputated limbs on which the limb prosthetic stocking is to be worn.

Preferred embodiments of the method and of the compression knitted fabric are disclosed herein.

With the method according to the invention, an at least substantially tubular compression knit extending from an open proximal end to a closed distal end can be manufactured, wherein a first tubular section of a stitch-forming basic knitted fabric is knitted from at least one knit yarn along a knitting direction extending from the proximal end to the distal end of the compression knit with a plurality of rows of stitches following in succession in the knitting direction, wherein an elastic weft yarn is bound into the stitches of the basic knitted fabric in each row of stitches or in every $n^{th}$ row of stitches with $n \in \mathbb{N}$ and $n \geq 2$ by tuck stitches, and subsequently a second section is knit seamlessly onto the first section of the basic knitted fabric from the at least one knit yarn along the knitting direction, wherein in the second section the number of stitches is successively reduced at least in some or all of the successive rows of stitches by transferring stitches, thereby a dome-shaped closed end is formed in the second section of the basic knitted fabric towards the distal end by reducing the number of stitches.

The reduction of stitches in the second section gives the second section a shape progressively tapering towards the distal end. The number of stitches in the circumferential direction of the tubular knitted fabric in the second section is successively reduced by overhanging of stitches in every row of stitches or only in selected rows of stitches, e.g. in every second, third or fourth row of stitches, so that the circumference of the tubular knitted fabric in the knitting direction, i.e. from the open proximal end to the closed distal end, becomes successively smaller, i.e. from the open proximal end to the closed distal end, until only a single stitch remains in the last knitted row of stitches at the distal end of the compression knitted fabric, which is knitted off on a needle of a flat knitting machine to fix the knitted fabric.

By successively reducing the circumference of the tubular knitted fabric in the second section, a dome-shaped closed end is formed at the distal end of the compression knitted fabric. This dome-shaped end forms a closed distal end in a prosthetic stocking made from the compression knit, designated for receiving the end of an amputated limb of a patient, as for example a leg stump.

By reducing the number of stitches in the second section of the compression knit, the shape of this second section can be adapted precisely to the body shape of the amputated limb. For this purpose, the amputated limb can be scanned, for example by an imagine device, and the number of stitches in the individual rows of stitches of the second section of the compression knit can be adapted to the detected circumferential course of the limb in its longitudinal direction. In a corresponding manner, the number of stitches of the basic knit in the first section of the compression knit can also be adapted to the circumferential course of the body extremity. In this way, a compression article individually adapted to the shape of the limb of a patient, for example an individually adapted stocking, can be produced.

Since an elastic weft yarn is bound into the basic knitted fabric during the manufacturing process, the compression pressure generated by the compression knitted fabric on a limb can be precisely adjusted. The compression pressure depends on the tension of the elastic weft yarn with which it is bound into the basic knitted fabric. The elastic weft yarn can be bound in the knitted fabric by forming tuck stitches. The stretchability of the knitted fabric (and thus the compression pressure that can be generated on a limb) can be adjusted by the tension of the weft yarn and/or via the length of the tuck stitches. By incorporating the elastic weft yarn into the basic knitted fabric with a variable yarn tension, it is thus possible, in particular, to generate a predefined pressure profile of the compression pressure exerted by the compression knitted fabric when applied to a limb with a gradual pressure profile. Preferably, the pressure profile at the distal end of the first section of the compression knit (or at the proximal end of the second section immediately adjacent thereto) has a higher compression pressure than at the proximal end of the compression knit.

Preferably, the weft yarn is bound in both the first section and the second section of the basic knitted fabric, whereby the weft yarn can be bound in, for example, in every row of stitches or in every $nt^h$ row of stitches with $n \in \mathbb{N}$ and $n \geq 1$ via tuck stitches. Preferably, a density of the weft yarn in the rows of the second section is smaller than a density of the weft yarn in the rows of the first section. The density of the weft yarn in the stitch rows of the basic knitted fabric can be varied, for example, by incorporating the weft yarn in every stitch row, to achieve a high density and only in every second, third or fourth stitch row, etc., to achieve a lower density. It is also possible to incorporate the weft yarn irregularly in the successive rows of stitches of the basic knitted fabric or to form irregular individual rows of stitches without incorporating the weft yarn. In this way, the generated pressure profile of the compression pressure can be varied along the knitting direction or along the longitudinal direction of a limb to which the compression knitted fabric is applied, because the generated compression pressure depends on the density of the weft yarn in the basic knitted fabric. Preferably, the density of the weft yarn in the dome-shaped end decreases compared to the (average) density in the other parts of the second section, in order to generate a lower compression pressure at the distal end of the compression knit, which, for example, comes into contact with the end of an amputated limb when used as a prosthetic stocking. This can prevent irritation at the very sensitive end of the limb stump.

Preferably, the knitting process is carried out in an uninterrupted manner on a flat knitting machine having a front needle bed and a rear needle bed, wherein the compression knitted fabric is knitted seamlessly by knitting a front ply of the compression knitted fabric on the front needle bed and a rear ply, which is opposite to the front ply, on the rear needle bed. Therein, the front ply and the rear ply are knitted seamlessly together by interchanging the at least one knitting yarn from the front needle bed to the rear needle bed, and vice versa, at the end sections of the front and rear needle beds. Thus, the side edges of the front ply and the rear ply are knitted together to form the tubular basic knitted fabric, into which the elastic weft yarn is bound by means of a weft yarn device of the flat knitting machine by forming tuck stitches. Due to the seamless knitting of the compression knitted fabric in an uninterrupted seamless knitting process, the produced compression knitted fabric obtains on the one hand a good wearing comfort, which avoids skin irritations at the body extremity of the wearer, and on the other hand the knitting process can be carried out very efficiently and quickly.

In particular, the stitch reductions in the second section of the compression knitted fabric can be effected in a very efficient manner by transfer operations with offsetting the needle beds of the flat knitting machine, whereby the needle beds can be offset with respect to each other by one, two or more needles. The number of stitches in the relevant row of stitches in the second section of the basic knitted fabric is reduced in accordance with the number of needles by which the two needle beds of the flat knitting machine are offset relative to one another during the respective transfer operation. The stitch reduction takes place in particular in selected stitch reduction zones between the edges of the front ply and the rear ply of the compression knitted fabric, which are each seamlessly knitted together with the edge of the respective opposite layer by transferring the knitting yarn from the front needle bed to the rear needle bed, and vice versa, at the end sections of the needle beds. In selected stitch courses having a higher number of stitch reductions, several such stitch reduction zones, at which the stitch reductions take place in a stitch course, are preferably arranged at a predefined distance from one another within a stitch row. In this way, the total number of stitch reductions within a row of stitches can be evenly distributed over the extend of the row of stitches in the circumferential direction of the tubular knitted fabric, resulting in a more uniform knitted pattern and avoiding bulges at the edges of the front and rear plies of the compression knitted fabric.

To fix the basic knit and to close the dome-shaped end, the knitting yarn can be knitted off once or several times at the distal end of the compression knit in the area of the last occupied needle of one of the two needle beds of the flat knitting machine.

To form a dome-shaped end of the basic knitted fabric, the number of stitch reductions in the rows of stitches of the second section preferably increases towards the distal end of the compression knitted fabric, as viewed in the knitting direction, until only one last needle remains on one of the needle beds of the flat knitting machine as an occupied needle and the knitting yarn is knitted off, one or more times, on this last needle to fix the distal end of the compression knitted fabric. In particular, in the rows of stitches of the dome-shaped end, in which a high number of stitch reductions take place, preferably a plurality of stitch reduction zones are provided, which are arranged at a distance from one another in a row of stitches.

To fix the weft yarn in the basic knitted fabric, the weft yarn is drawn from a weft yarn package and is conveniently locked in the basic knitted fabric at the distal end of the compression knitted fabric in the area of the last knitted stitches of the basic knitted fabric by several catching hooks and then the weft yarn is cut off from the weft yarn package. This ensures that the weft thread does not come loose from the basic knitted fabric.

The method according to the invention can be used to produce compression knitted fabrics, in particular for the production of knitted prosthetic stockings with a compressive effect, wherein the compression knitted fabric is comprising a stitch-forming basic knitted fabric with a plurality of successive rows of stitches and containing a tubular first section which is open at the proximal end and a second section which adjoins the first section in the knitting direction and is knitted seamlessly onto the first section. Therein, the second section is forming a dome-shaped closed end at the distal end of the compression knitted fabric, which end is formed in the second section by successively reducing the number of stitches at least in some or all of the successive stitch rows of the basic knitted fabric towards the distal end. An elastic weft yarn is bound in the basic knitted fabric, in particular in the first and in the second section, via tuck stitches.

Preferably, the compression knitted fabric is seamless overall. This prevents skin irritation and local pressure points that can occur in knitted fabrics with seams in the seam areas.

In a preferred embodiment, the basic knitted fabric is a right-left knit. However, other knitted structures can also be used to form the basic knitted fabric, e.g. a right-right knit.

The weft yarn can be included in the basic knitted fabric in every row of stitches or in every second, third or fourth, etc., row of stitches.

The knitting yarn can be, for example, a single wound spandex yarn or an elastic single yarn, a plied yarn or a twisted yarn. The weft yarn is preferably a double wound spandex yarn.

When applied to an amputated limb of a patient, the compression knitted fabric generates a compression pressure on the limb, preferably with a gradual pressure profile, whereby the compression pressure particularly increases gradually in the first section from the proximal end to the distal end of the compression knit. Towards the closed end, i.e. at the distal end of the compression knitted fabric, the generated compression pressure preferably decreases again. The compression pressure generated is at a maximum, for example, at the transition from the first section to the second section and decreases gradually in the second section towards the distal end of the compression knit. In this way, irritation of the sensitive end of the limb stump of an amputated limb caused by excessive compression in the second section, and in particular in the region of the closed end, can be avoided. This can be achieved, for example, by progressively decreasing the density of the weft yarn in the final rows of stitches of the basic knitted fabric towards the distal end. At the proximal end of the compression knit, a compression pressure of 10 mmHg to 30 mmHg is expediently and the maximum compression pressure is preferably less than 35 mmHg.

The compression knitted fabric according to the invention can be used to produce seamless compression articles for various medical indications, such as a prosthetic stocking for application to an amputated limb of a patient or a compressive head mask for application to the head of a patient. Depending on the use, the shape of the knitted fabric is adapted to the patient's body part, in particular by individual customization, for which purpose the shape of the body part is recorded, for example by means of a scanner or a camera. The recorded shape of the body part is taken into account in the manufacture process of the compression knitted fabric, for example by adjusting the circumferential profile of the tubular basic knitted fabric and the length of the knitted fabric in the knitting direction during the knitting process, or by omitting any openings (e.g. a facial opening in the case of a face mask) during the knitting process.

BRIEF DESCRIPTION OF THE DRAWINGS

These and other advantages as well as preferred features of the invention result from the embodiments described below with reference to the accompanying drawings, which serve to explain the invention and do not limit the scope of protection of the invention defined by the following claims. The drawings show:

FIGS. 1A-1C: An illustration of knitting patterns in the form of a technical cartridge of a first embodiment of the compression knitted fabric according to the invention, wherein FIG. 1A shows the first seven courses of stitches, FIG. 1B shows the subsequent courses 8 to 16 of stitches and FIG. 1C shows the courses 17 to 27 of stitches terminating the knitted fabric in the direction of knitting;

FIG. 5: the symbols used in FIGS. 1A-1C, 2, and 3 to represent the knitted weaves of a knitting yarn T and an elastic weft yarn S, wherein the designations "front" and "rear" are referring to the front needle bed and the rear needle bed of a flat knitting machine on which the compression knitted fabric is knitted.

DETAILED DESCRIPTION

Figure 1A:
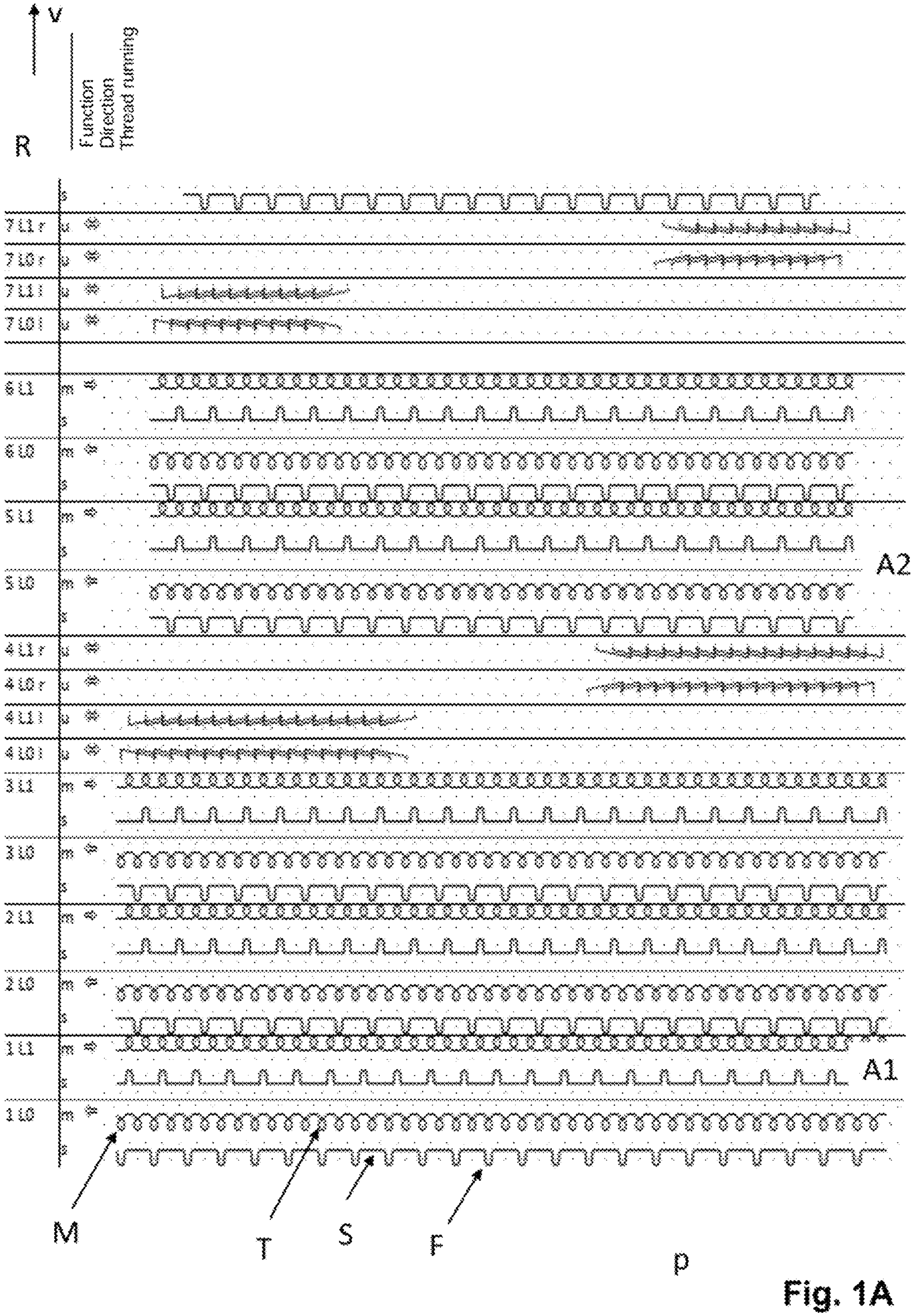
Figure 1B:
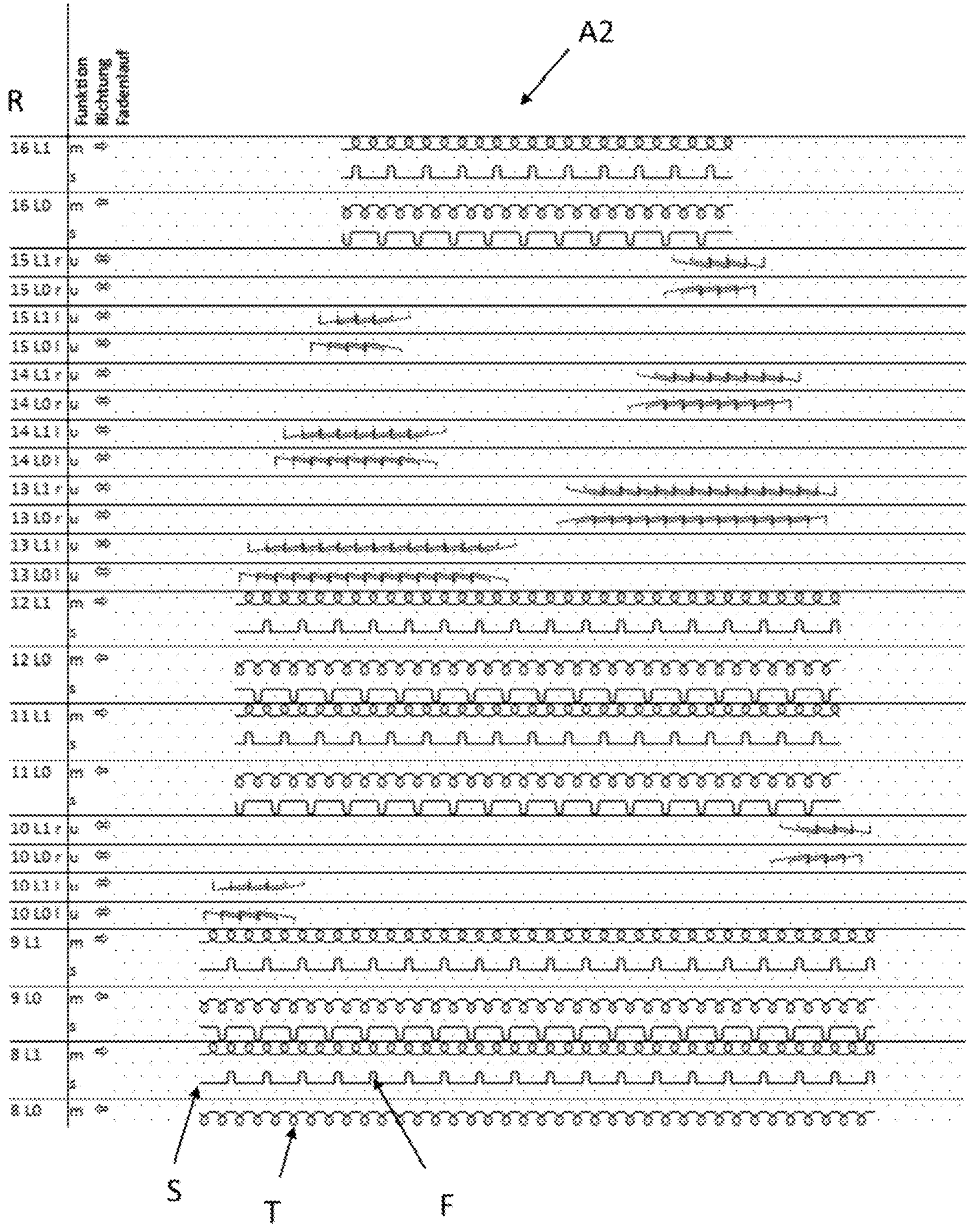
Figure 1C:
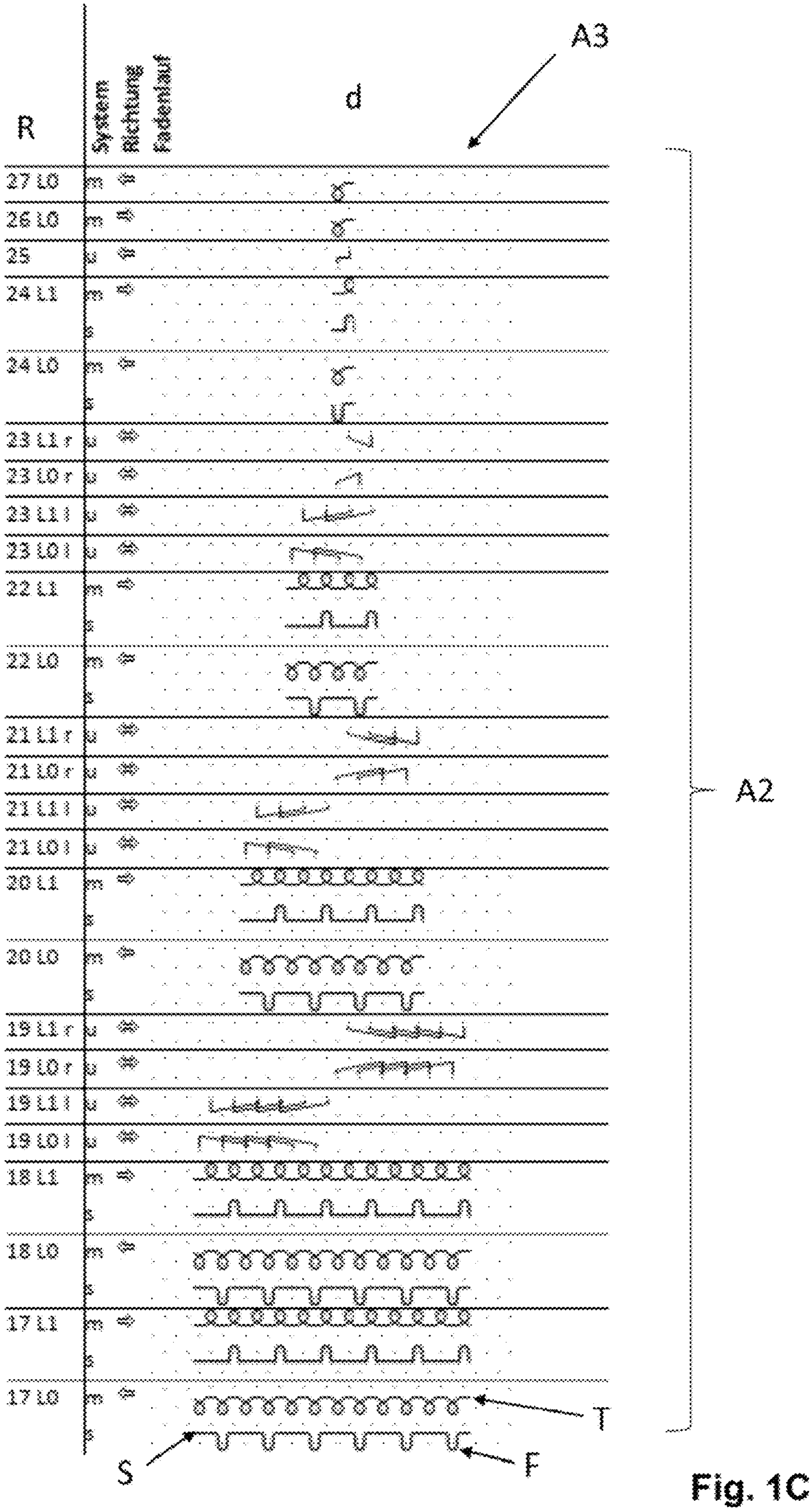

FIGS. 1A-1C show the yarn path of a first embodiment of the compression knitted fabric according to the invention by means of a technical cartridge, wherein the compression knitted fabric shown in FIGS. 1A-1C comprises a total of 27 stitch rows R following one another in a knitting direction v, which are divided in the partial images of FIGS. 1A-1C, wherein FIG. 1A shows the stitch rows 1 to 7, FIG. 1B shows the stitch rows 8 to 16 and FIG. 1C shows the stitch rows 17 to 27.

The compression knitted fabric shown in FIGS. 1A-1C is knitted seamlessly and without interruption in a continuous knitting process on a flat knitting machine with a front needle bed and a rear needle bed, wherein a front ply L0 of a basic knitted fabric M is knitted on the front needle bed and a rear ply L1 opposite the front ply is knitted on the rear needle bed from a knitting yarn T. The front ply is knitted seamlessly together with the rear ply by interchanging the knitting yarn T at the edges of the front and rear layers from an end sections of the front needle bed to a beginning section of the rear needle bed, and vice versa, to form a tubular basic knitted fabric M. The front ply is designated "L0" in the technical cartridge of FIGS. 1A-1C in the respective row of stitches (in the left column next to the row number R), and the back ply is designated as "L1" in each row of stitches. The front ply L0 and the rear ply L1 form a tubular basic knitted fabric M by knitting the side edges of the front ply L0 with the side edges of the rear ply in the same row of stitches and by joining the edges of the rear ply L1 with the edges of the front ply L0 of the following row of stitches. In FIGS. 1A-1C, the direction of movement of the yarn guide along the needle beds of the flat knitting machine is indicated by an arrow in the "Direction" column. As can be seen, for example, from FIG. 1A in row 1, when knitting the front ply L0, the yarn guide runs on the front needle bed from right to left, and in the rear ply L1 of the same row of stitches (row 1), the yarn guide runs on the rear needle bed from left to right, and so on. In this process, the knitting yarn T, from which the basic knitted fabric M is knitted, is knitted into a stitch m on each needle of one of the two needle beds of the flat knitting machine. The stitch formations of the knitting yarn T are each designated with the symbol "m" in the "Function" column of FIGS. 1A-1C. In alternative embodiments, the knitting yarn T can also be knitted to form a stitch m on, for example, every second needle of the front and rear needle beds of the flat knitting machine and floated over intermediate needles. Other structures of the basic knitted fabric are also possible, with the knitting yarn T forming the basic knitted structure in particular by a combination of stitch, float or stitch on each needle of the front and rear needle beds of the flat knitting machine. The knitting yarn T may be, for example, a single wound spandex yarn or a single yarn. The knitting yarn T can also be a double yarn or a plied yarn. In addition to the knitting yarn T, an additional yarn can also be bound into the basic knitted fabric M by plating, wherein the knitting yarn T is lying on the right side of the fabric while the additional yarn (plated yarn) lies on the left side of the fabric.

An elastic weft yarn S is bound into the basic knitted fabric M formed from the knitting yarn T by means of a weft yarn device of the flat knitting machine. In the example shown in FIGS. 1A-1C, a weft thread S is bound into each row R of stitches. Alternatively, the elastic weft yarn S can also be incorporated into the basic knitted fabric M only in every second, third or fourth row of stitches R. Non-periodic sequences are also possible in that the elastic weft yarn S is, for example, first inserted in three successive rows of stitches, omitted in a fourth row of stitches, inserted in the following fifth row of stitches and omitted again in the following sixth row of stitches. The weft yarn S can, for example, be a double-wound spandex thread.

Figure 2:
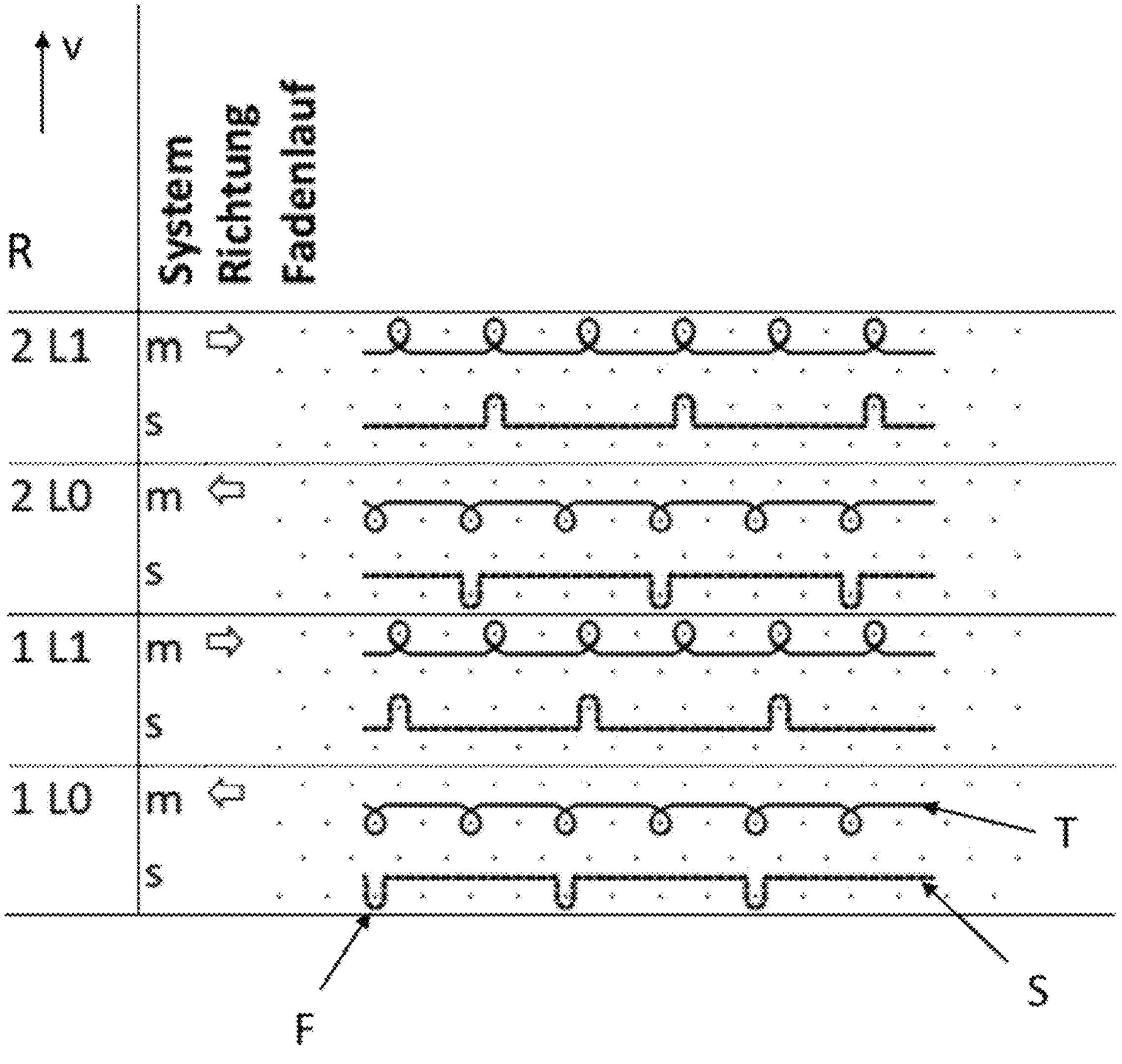
FIG. 2: an illustration of a knitting pattern in the form of a technical cartridge of a second embodiment of the compression knitted fabric according to the invention, wherein the first two rows of stitches of a first section of the knitted fabric are shown as an example in FIG. 2.
Figure 3:
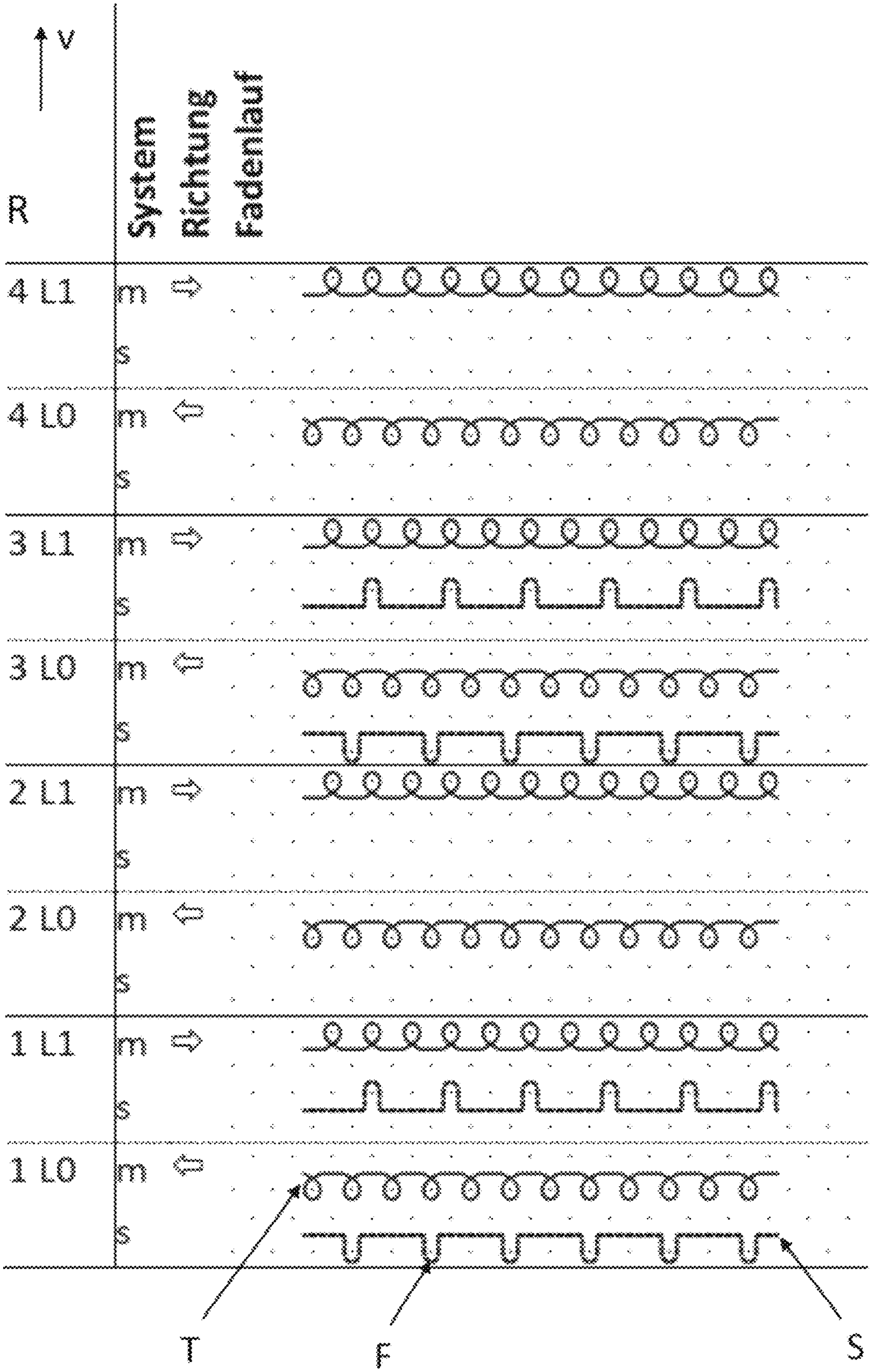
FIG. 3: an illustration of a knitting pattern in the form of a technical cartridge of a third embodiment of the compression knitted fabric according to the invention, wherein the first four rows of stitches of a first section of the knitted fabric are shown as an example in FIG. 3.

The integration of the elastic weft yarn S into the basic knitted fabric M, which is indicated in the "Function" column of the drawings in FIGS. 1A-1C, 2, and 3 by the symbol "s" in each case, is achieved by means of tuck stitches F which are produced on certain needles of the front and rear needle beds of the flat knitting machine in the weft yarn system S. The weft yarn S lies float between two tuck stitches F of the weft yarn S which follow one another in the direction of the row of stitches. In the knitting pattern shown in FIGS. 1A-1C, the weft yarn S forms a tuck stitch F on every second needle of the front and rear needle beds of the flat knitting machine and accordingly lies float on every second needle lying in between. Other bindings of the elastic weft yarn S into the basic knitted fabric M are possible, as shown in FIGS. 2 and 3. The example of the compression knitted fabric shown in FIGS. 1A-1C is a right-/left basic knitted fabric M with weft yarn S integrated 1:1 via tuck stitches F.

The knitting direction v shown in FIGS. 1A-1C runs from a proximal end p to a distal end d of the compression knitted fabric. In FIGS. 1A-1C the proximal end p is shown in the first row of stitches 1 and the distal end d in FIG. 1C is shown in the last row of stitches (row 27). The proximal end p of the compression knitted fabric of FIGS. 1A-1C forms an open end of a tubular first section A1 and the distal end d forms a dome-shaped closed end A3 of the knitted fabric.

The first section A1, which is shown in FIG. 1A, comprises the first three rows 1 to 3 of the knitted fabric and forms a tubular knitted fabric which comprises a certain number of stitches m of the knitting yarn T on the front needle bed and the rear needle bed of the flat knitting machine and has a constant (or changing) number of stitches m in the successive rows of stitches of the first section A1 along the knitting direction v. However, the first section A1 of the compression knit may comprise further rows of stitches each having a constant or changing number of stitches m along the knitting direction v in each row of stitches R, which are not shown here in the drawings. The number of stitches m in the individual rows of stitches R of the first section A1 can thereby be different in order to adapt the contour of the tubular first section A1 to the body shape of a body extremity to which the compression knitted fabric (for example in the form of a stocking) is to be applied. The change in the number of stitches in the individual rows of stitches R of the first section A1 can be effected for this purpose in particular by stitch increases or stitch decreases, which are expediently effected at the edges of the front ply L0 and the rear ply L1 of the basic knitted fabric M.

The first, tubular section A1 of the basic knitted fabric M is followed in the knitting direction v towards the distal end d of the compression knitted fabric, by a second section A2 with a contour tapering towards the distal end d. In the embodiment shown in FIGS. 1A-1C, the elastic weft yarn S comprises rows of stitches 4 to 27. In the embodiment shown in FIGS. 1A-1C, the second section A2 comprises the stitch rows 4 to 27. The elastic weft yarn S is thereby integrated, both in the first section A1 and in the second section A2, of the basic knitted fabric M, whereby in the embodiment shown, the integration of the weft yarn S in the first section A1 and in the second section A2 is uniform, i.e., in both sections A1 and A2, the elastic weft yarn S is integrated into the basic knitted fabric M in each row of stitches via tuck stitches F on every second needle of the needle beds of the flat knitting machine.

The extension of the compression knitted fabric in the circumferential direction, i.e. in the direction of the rows of stitches of the knitted fabric, is successively reduced in the second section A2 of the compression knitted fabric by stitch reduction by means of transferring the knitting yarn T using a transfer device. The transfer of the knitting yarn T is indicated by the symbol "u" in the "Function" column of FIGS. 1A-1C. The transfer u of the knitting yarn T in selected stitch rows R of the basic knitted fabric M results in a stitch reduction MM, i.e. a reduction in the number of stitches of the knitting yarn T in the relevant stitch row by a predetermined number of stitches. In the example shown in FIGS. 1A-1C, the stitch reduction takes place, for example, in row 4 of the knitted fabric both on the front needle bed and on the rear needle bed of the flat knitting machine, both in the front ply L0 and in the rear ply L1 of the knitted fabric as well. The needles of the front and rear needle beds of the flat knitting machine, on which the knitting thread T is transferred by the transfer device to reduce the number of stitches, are identified in row 4 of the knitted fabric by the clip symbols shown there. Each clip symbol symbolizes a transfer u of the knitting yarn T by a predetermined number of needles inwards, i.e. against the original direction of movement of the thread guide, which is why a double arrow is drawn in the "Direction" column of FIGS. 1A-1C in each of the rows of the knitted fabric in which a transfer u of the knitting yarn T takes place. Such an overhanging u of the knitting yarn T takes place in rows 4, 7, 13 to 15, 19, 21, 23 and 25 in the embodiment shown in FIGS. 1A-1C. The stitch reduction allows the contour of the knitted fabric to be adjusted along the knitting direction v, i.e. from the proximal end p to the distal end d.

The stitch reductions in the selected rows of stitches of the knitted fabric are carried out by overhanging u the knitting yarn T from the active needle bed of the flat knitting machine to the opposite needle bed, which is currently inactive, and a subsequent shifting of the inactive needle bed relative to the active needle bed by a predetermined number of needles. After the mutual displacement of the two opposing needle beds, the stitches of the knitting yarn T are hooked from the inactive needle bed back onto the active needle bed, whereby, due to the displacement of the opposing needle beds, a stitch reduction, i.e. a reduction in the number of stitches in the relevant row of stitches, takes place depending on the number of needles by which the two needle beds have been displaced relative to one another. The stitch reductions take place in selected stitch reduction zones MM within selected rows of stitches, the stitch reduction zones MM being arranged between the edges of the front ply L0 or the rear ply L1. Preferably the reduction zones MM are at a distance from the edges of the front ply or the rear layer. Several such stitch reduction zones MM can also be arranged at a distance from one another within a row of stitches.

The number of stitches reduced in this way in the stitch reduction zones MM can be controlled by the offset of the two opposing needle beds relative to one another. In the example shown in FIGS. 1A-1C, for example, the needle beds are offset with respect to each other by two needles. However, an offset by only one needle or by three, four or more needles can take place as well, with a corresponding number of stitch reductions by one stitch or by three, four or more stitches, etc., in the relevant row of stitches in which a stitch reduction takes place by overhanging u of the knitting yarn.

The stitch reductions in the selected rows of the knitted fabric to stitches of the basic knitted fabric lying further inside can also be carried out by overhanging u the knitting yarn T from the active needle bed of the flat knitting machine to an auxiliary needle bed.

The overhanging u of the knitting yarn T takes place in each case at the edge of the relevant row of stitches R, i.e. either at the left edge 1 or at the right edge r, as can be seen from rows 4, 7, 13 to 15, 19, 21 and 23 of the knitting diagram in FIGS. 1A-1C. The overhanging u of the knitting yarn T thus takes place either at the left edge 1 of the front ply L0 and at the left edge of the rear ply L1 connected to the front ply L0, or at the right edge r of the front ply L0 and at the right edge r of the rear ply L1 connected thereto. The respective side edges of the front ply L0 and the rear ply L1 are joined together in this case by guiding the knitting yarn T from the front needle bed onto the rear needle bed of the flat knitting machine, and vice versa, in order to join the front ply L0 to the rear ply L1 together to form a closed tubular fabric.

By reducing the number of stitches in selected stitch rows R of the knitted fabric, the extent of the knitted fabric in the direction of the stitch rows can be varied along the knitting direction v, and the contour of the knitted fabric can thereby be optimally adapted to the body shape of a body extremity to which the compression knitted fabric is to be applied in order to exert a defined compressive effect. The number of stitches in the individual stitch rows R of the knitted fabric required for optimum adaptation of the shape of the knitted fabric to the body shape of the body extremity can be determined by scanning the body shape of the limb and subsequently calculating the necessary number of stitches in the individual stitch rows R depending on the shape of the limb.

In the second section A2 of the compression knitted fabric, which in the embodiment of FIGS. 1A-1C extends over the stitch rows 4 to 27, the number of stitches m in at least some selected stitch rows R (in the embodiment of FIGS. 1A-1C these are stitch rows 4, 7, 10, 13 to 15, 19, 21, 23 and 25) by overhanging u stitches m of the basic knitted fabric M, whereby the extension of the basic knitted fabric M in the direction of the rows of stitches along the knitting direction v, i.e. towards the distal end d of the knitted fabric, is successively reduced due to the stitch reduction. This results in a dome-shaped closed end A3 at the distal end d of the knitted fabric. In the knitted fabric shown in FIGS. 1A-1C and in particular in FIG. 1C, the dome-shaped closed end A3 extends from course 23 to the last course 27. In course 23, the knitting yarn T in the front ply L0 and in the rear ply L1 is initially transferred by two stitches in each case, and then the knitting yarn T in course 23 is transferred at the right edge r of the front ply L0 and of the rear ply L1 by one stitch in each case. In the following row of stitches 24, the knitting yarn T is knitted on both the front ply L0 and the rear ply L1 (i.e. on the front and rear needle beds of the flat knitting machine) to form a single remaining stitch m, and the elastic weft yarn S is bound into this stitch m by a tuck stitch F. In the following row of stitches 25, a final overhanging u of the knitting yarn T is effected by means of the transfer device by one stitch m from the rear needle bed (i.e. from the rear needle bed) to the front needle bed (i.e. onto the front needle bed). In the last two rows of stitches 26 and 27, the knitting yarn T is knitted off to form a stitch m on the front needle bed (i.e. in the front ply L0 of the knitted fabric). The knitting yarn T can be knitted off as often as required in a last, remaining stitch m on the front needle bed of the flat knitting machine. Multiple knitting-off ensures that the knitted fabric does not come loose at the closed, distal end d. The elastic weft yarn S is locked at this point by one or more knitted structures in the basic knitted fabric M, in particular by tuck stitches F or by stitch formation, and then the weft yarn is cut off by a weft yarn roller integrated in the weft yarn device, from which the weft yarn S is drawn off.

In this way, a tubular compression knitted fabric with an elastic weft yarn S, which is bound into the basic knitted fabric M, can be produced with a precisely defined pressure profile of the compression pressure exerted by the compression knitted fabric on a body extremity (limb) of a patient, wherein the tubular knitted fabric has an open proximal end p and a closed distal end d. The compression pressure exerted by the knitted fabric, when applied to a body extremity (limb) can thereby be controlled by the yarn tension of the weft yarn S, with which the latter is bound into the basic knitted fabric, and by the length of the tuck stitches F, by which the weft yarn S is bound into the basic knitted fabric. Preferably, at least in the first section A1, the compression knitted fabric generates a compression profile with decreasing pressure towards the proximal end p. Such a compression knitted fabric is particularly suitable for use as a compression stocking or as a compression head mask.

When used as a head mask, a face opening is knitted into the tubular knitted fabric of the first section A1. This can be done by reducing stitches in selected rows of stitches of the first section A1. When used as a stocking, in particular a prosthetic stocking, to be used on an amputated limb, the pressure gradient in the second section A2 may decrease towards the distal end d to prevent excessive pressure at the distal end of the amputated limb. In this example of use, the knitted fabric exhibits a maximum of compression pressure at the transition from the first section A1 to the second section A2.

FIG. 2 shows the yarn course of a second embodiment of the compression knitted fabric according to the invention by means of a technical cartridge, wherein the compression knitted fabric shown exemplarily in FIG. 2 shows two stitch rows R (row 1 and row 2) of the first section A1, in which the basic knitted fabric M is formed as a right-hand/left-hand multi-eye knitted fabric with an elastic weft yarn S bound therein in each row R. Therein, the weft yarn S, in contrast to the embodiment of FIGS. 1A-1C, is bound into the basic knitted fabric M on every fourth needle of the needle beds of the flat knitting machine via a tuck stitch F and is floated over three needles between two neighboring tuck stitches F which follow one another in a row of stitches R. The two rows of stitches shown in FIG. 2 are followed by correspondingly constructed rows of stitches of the second section A2, in which stitch reductions are effected in selected stitch reduction zones MM in accordance with the embodiment of FIGS. 1A-1C by means of the above-described overhanging u of the knitting yarn T.

FIG. 3 shows the yarn course of a third embodiment of the compression knitted fabric according to the invention by means of a technical cartridge, wherein the compression knitted fabric shown exemplarily in FIG. 3 shows four stitch rows R (rows 1 to 4) of the first section A1 of the compression knitted fabric according to the invention, wherein the basic knitted fabric M is constructed as a right-hand/left-hand knitted fabric with an elastic weft yarn S bound therein in every second row R. The weft yarn S, as in the embodiment of FIGS. 1A-1C, is bound into the basic knitted fabric M on every second needle of the needle beds of the flat bed knitting machine via a tuck stitch F and is lying float over a needle between two neighboring tuck loops F which follow one another in a row of stitches R. In the embodiment shown in FIG. 3, the weft yarn S is bound into the odd-numbered rows R (rows 1, 3, etc.) of the basic knitted fabric M and there is no weft yarn in the even-numbered rows (rows 2, 4, etc.). The four rows of stitches shown in FIG. 3 are followed by correspondingly formed rows of stitches of the second section A2, in which stitch reductions are made in selected stitch reduction zones MM in accordance with the embodiment of FIGS. 1A-1C by means of the above-described overhanging u of the knitting yarn T.

Figure 4:
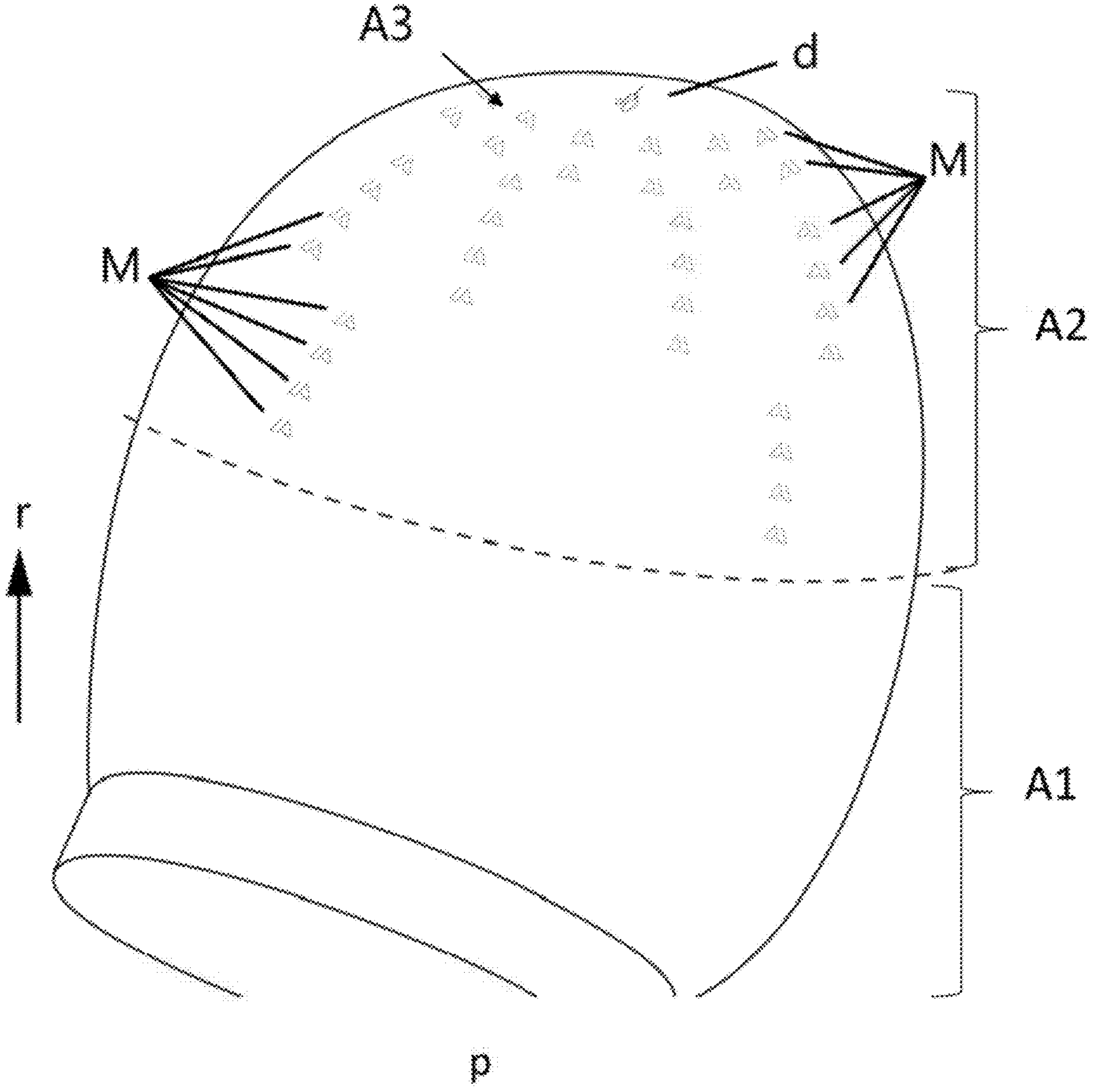
FIG. 4: a photographic representation of a prosthetic stocking made of a compression knitted fabric according to the invention.

FIG. 4 shows a limb stump stocking (prosthetic stocking) for applying to an amputated body extremity (limb), e.g. to an amputated leg. The stocking is made from a compression knitted fabric according to the invention, which is knitted along the knitting direction v from a proximal end p to a distal end d and comprises a tubular first section A1 with an opening at the proximal end p and an adjoining second section A2 with a dome-shaped closed end A3 at the distal end d. The second section A3 contains stitch reduction zones MM formed by the above-described overhanging processes during knitting. The second section A3 contains stitch reduction zones MM formed by the above-described overhanging processes during knitting, which can be seen in the knitted fabric on the outer fabric side and are designated by the symbol "MM" in FIG. 4. Towards the distal end d, the circumference of the second section A2 with the closed end A3 arranged at the distal end d tapers further and further, caused by the stitch reductions in the stitch reduction zones MM, until the last stitch at which the knitting yarn (and thus the basic knitted fabric knitted from the knitting yarn) is fixed by a multiple knitting-off.

The invention claimed is:

1. A method for producing an at least substantially tubular compression knitted fabric for producing knitted prosthetic stockings for application to an amputated limb of a patient for supplying a compressive force onto the amputated limb, the compression knitted fabric extending from an open proximal end to a closed distal end, wherein:

a basic knitted fabric forming stitches from at least one knitting yarn along a knitting direction extending from the open proximal end to the closed distal end of the compression knitted fabric is knitted seamlessly in an uninterrupted knitting operation on a flat knitting machine having a front needle bed and a rear needle bed, the front and rear needle beds extending between end sections thereof, wherein a front ply of the basic knitted fabric is knitted on the front needle bed and a rear ply opposite the front ply is knitted on the rear needle bed, the front ply and the rear ply each having side edges, the front ply and the rear ply seamlessly knitted together at their respective side edges by interchanging the at least one knitting yarn from the front needle bed onto the rear needle bed, and vice versa, at the respective end sections of the front and rear needle beds, to form a tubular basic knitted fabric having a plurality of rows of stitches following one another in the knitting direction, wherein an elastic weft yarn is drawn off from a weft yarn package during knitting and is bound into the basic knitted fabric by a weft yarn device of the flat knitting machine by forming tuck stitches, a tubular first section of the compression knitted fabric forming stitches from the at least one knitting yarn is knitted along the knitting direction with a plurality of rows of stitches following one another in the knitting direction, wherein the elastic weft yarn is bound into the stitches of the tubular first section of the basic knitted fabric via tuck stitches, a second section of the compression knitted fabric is seamlessly knitted onto the first section of the compression knitted fabric along the knitting direction, wherein in the second section as viewed in the knitting direction, a number of stitches is successively reduced at least in some or in all of successive rows of stitches of the second section by transferring of stitches, as a result of which a closed dome-shaped end is formed at the closed distal end of the compression knitted fabric by a reduction of stitches, wherein the knitting yarn is knitted off once or several times at the closed distal end of the compression knitted fabric in a region of a last occupied needle of one of the front and rear needle beds of the flat knitting machine, in order to close the dome-shaped end, and wherein the elastic weft yarn is interlocked in the basic knitted fabric at the closed distal end of the compression knitted fabric by one or more binding elements, and the elastic weft yarn subsequently is cut off from the weft yarn package after it has been interlocked in the basic knitted fabric.

2. The method according to claim 1, wherein the reduction of stitches in the second section of the compression knitted fabric is affected by an offset of the front and rear needle beds of the flat knitting machine with respect to each other, wherein the offset of the front and rear needle beds is affected by one or more needles.

3. The method according to claim 2, wherein the reduction of stitches takes place in selected stitch reduction zones in at least one of the front ply and the rear ply of the compression knitted fabric between the side edges of the front ply and the rear ply.

4. The method according to claim 3, wherein, in selected courses having a higher number of reduction of stitches, a plurality of stitch reduction zones is arranged at a predetermined distance from one another within each course of the selected courses.

5. The method according to claim 1, wherein the elastic weft yarn is bound into the stitches of the basic knitted fabric in each row of stitches or in every $n^{th}$ row of stitches, with $n \in N$ and $n \geq 2$, wherein a density of the elastic weft yarn in the rows of stitches of the second section is smaller than a density of the elastic weft yarn in the rows of stitches of the first section.

6. The method according to claim 4, wherein each stitch reduction zone is arranged at a predetermined distance from the side edges of the front ply and the rear ply.

7. A method for producing an at least substantially tubular compression knitted fabric for producing knitted prosthetic stockings for application to an amputated limb of a patient for supplying a compressive force onto the amputated limb, the compression knitted fabric extending from an open proximal end to a closed distal end, wherein:

a basic knitted fabric forming stitches from at least one knitting yarn along a knitting direction extending from the open proximal end to the closed distal end of the compression knitted fabric is knitted seamlessly in an uninterrupted knitting operation on a flat knitting machine having a front needle bed and a rear needle bed, the front and rear needle beds extending between end sections thereof, wherein a front ply of the basic knitted fabric on the front needle bed and a rear ply opposite the front ply is knitted on the rear needle bed, the front ply and the rear ply each having side edges, the front ply and the rear ply are seamlessly knitted together at their respective side edges by interchanging the at least one knitting yarn from the front needle bed onto the rear needle bed, and vice versa, at the respective end sections of the front and rear needle beds, to form a tubular basic knitted fabric with a plurality of rows of stitches following one another in the knitting direction, wherein an elastic weft yarn is drawn off from a weft yarn package during knitting and is bound into the basic knitted fabric by a weft yarn device of the flat knitting machine by forming tuck stitches, a tubular first section of the compression knitted fabric forming stitches from the at least one knitting yarn along the knitting direction and extending from the open proximal end to the closed distal end of the compression knitted fabric is knitted, with a plurality of rows of stitches following one another in a knitting direction, wherein the elastic weft yarn is bound into the stitches of the tubular first section of the basic knitted fabric via tuck stitches, a second section of the compression knitted fabric is seamlessly knitted onto the first section of the basic knitted fabric along the knitting direction, wherein in the second section, as viewed in the knitting direction, a number of stitches is successively reduced at least in some or in all of the successive rows of stitches of the second section by transferring of stitches as a result of which a closed dome-shaped end is formed at the closed distal end of the compression knitted fabric by a reduction of stitches, wherein the elastic weft yarn is bound into the stitches of the basic knitted fabric in each row of stitches or in every $n^{th}$ row of stitches, with $n \in N$ and $n \geq 2$, wherein a density of the elastic weft yarn in the rows of stitches of the second section is smaller than a density of the elastic weft yarn in the rows of stitches of the first section, wherein the elastic weft yarn is interlocked in the basic knitted fabric at the closed distal end of the compression knitted fabric by one or more binding elements, and wherein the elastic weft yarn is cut off from the weft yarn package after it has been interlocked into the basic knitted fabric.

* * * * *